United States Patent [19]

Ilvespää et al.

[11]  3,941,804
[45]  Mar. 2, 1976

[54] 1-HETEROARYLSULPHONYL-2-IMINO-IMIDAZOLIDINES

[75] Inventors: Atso Ilvespää, Allschwil; André Gagneux; Ernst Schweizer, both of Basel; Jörg Frei, Schonenbuch, all of Switzerland

[73] Assignee: Ciba-Geigy Corporation, Ardsley, N.Y.

[22] Filed: July 15, 1974

[21] Appl. No.: 488,879

[30] Foreign Application Priority Data
July 27, 1973  Switzerland.................... 10998/73
Apr. 10, 1974  Switzerland.................... 5067/74

[52] U.S. Cl..... 260/309.7; 260/243 R; 260/248 AS; 260/248 R; 260/250 A; 260/250 R; 260/256.4 R; 260/294.8 F; 260/302 A; 260/302 D; 260/302 H; 260/307 G; 260/307 H; 260/307 R; 260/308 A; 260/308 D; 260/308 R; 260/309; 260/332.2 R; 424/246; 424/249; 424/250; 424/263; 424/269; 424/270; 424/272; 424/273

[51] Int. Cl.$^2$.......................................... C07D 49/34

[58] Field of Search................... 260/309.7

[56] References Cited
UNITED STATES PATENTS
3,538,035  11/1970  Dietrich..................... 260/309.7 X
3,812,144  5/1974  Dietrich........................ 260/309.7

*Primary Examiner*—Ethel G. Love
*Attorney, Agent, or Firm*—Joseph G. Kolodny; John J. Maitner; Theodore O. Groeger

[57] ABSTRACT

Compounds of the class of 1-heteroarylsulphonyl-2-imino-imidazolidines which are substituted in the 3-position by an aliphatic or cycloaliphatic hydrocarbon radical, especially a cycloalkyl radical, and their pharmaceutically acceptable acid addition salts have valuable pharmacological properties. In particular, they possess hypoglycaemic activity and can be used for the treatment of hyperglycaemia in mammals. A specific embodiment is 1-[5-(2-butyramido-ethyl)-2-thienylsulphonyl]-2-imino-5-cyclohexyl-imidazolidine.

5 Claims, No Drawings

1-HETEROARYLSULPHONYL-2-IMINO-IMIDAZOLIDINES

DETAILED DESCRIPTION

The present invention relates to new imidazolidine derivatives and their acid addition salts having valuable pharmacological properties, and pharmaceutical compositions containing these compounds, and the use of these new compounds.

The new imidazolidine derivatives, according to the invention, correspond to the formula I

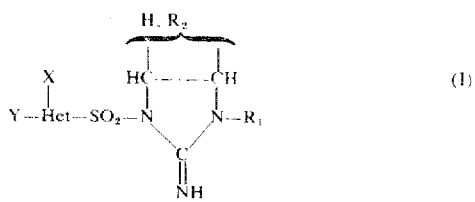

in which
- Het denotes a heteroaromatic radical with 5 to 6 ring members including, as the hetero atoms, either 1 to 4 nitrogen atoms, or 1 oxygen atom together with 0 to 2 nitrogen atoms, or 1 sulphur atom together with 0 to 2 nitrogen atoms,
- $R_1$ denotes an alkyl group with at most 12 carbon atoms, an alkenyl group with 3 to 5 carbon atoms, a cycloalkyl, lower alkyl-cycloalkyl, cycloalkenyl or lower alkyl-cycloalkenyl group, each of which of at most 7 carbon atoms, or 7 to 9 carbon atom,
- $R_2$ denotes hydrogen, or the methyl or ethyl group,
- X, which is only present if Het contains not more than three nitrogen atoms alone or one nitrogen atom together with one oxygen or sulphur atom as ring members, denotes hydrogen, halogen up to atomic number 35, an alkyl group which is or is not interrupted by 1 or by 2 non-adjacent oxygen or sulphur atoms and contains a total of at most 7 carbon atoms, or the hydroxyl group, the amino group or an alkanamido group with at most 4 carbon atoms, and
- Y has the meaning of X or denotes a radical of the partial formula Ia or Ib

in which
- $m$ denotes 2 or 3,
- Z denotes oxygen or sulphur,
- $R_3$ denotes hydrogen or the methyl group,
- $R_4$ denotes an alkyl or chloroalkyl group with at most 7 carbon atoms, an alkenyl group with 2 to 5 carbon atoms, a cycloalkyl, lower alkyl-cycloalkyl, cycloalkenyl or lower alkyl-cycloalkenyl group, each of which with a total of at most 8 carbon atoms, a phenyl group, a phenylalkyl group of 7 to 10 carbon atoms or a phenylalkenyl group of 8 to 10 carbon atoms, whereby the phenyl group present as $R_4$ or as a part of $R_4$ is unsubstituted or substituted by one to three substituents selected from the group consisting of halogen up to atomic number 35, trifluoromethyl, alkyl with at most 4 carbon atoms, hydroxy, alkoxy with at most 2 carbon atoms and aklylthio with at most 2 carbon atoms, or $R_4$ denotes a pyridyl, thienyl or furyl group, or said heterocyclic radicals substituted by methyl; addition salts of compounds of the formula I with inorganic or organic acids are also a subject of the invention.

In the compounds of the formula I, the symbols which follow can be, for example: Het, as a heteroaromatic radical with 5 to 6 ring members, i.e. a 5- to 6-membered heterocyclic radical in its lowest stage of hydrogenation, pyrrolyl, pyrazolyl, imidazolyl, v-triazolyl, s-triazolyl, tetrazol-5-yl, pyridyl, pyridazinyl, pyrimidinyl, pyrazinyl, s-triazinyl, as-triazinyl, furyl, 2H- or 4H-pyranyl, oxazolyl, isoxazolyl, 1,2,4-oxadiazolyl, 1,3,4-oxadiazolyl, thienyl, 2H- or 4H-thiopyranyl, thiazolyl, isothiazolyl, 1,2,4-thiadiazolyl, 1,3,4-thiadiazolyl, 2H-, 4H- or 6H-1,3-thiazinyl or the 2H- or 4H-1,4-thiazinyl radical; $R_1$, as an alkyl group with at most 12 carbon atoms, the methyl, ethyl, propyl, isopropyl, butyl, sec.butyl, tert.butyl, isobutyl, pentyl, isopentyl, 2,2-dimethylpropyl, 1-methylbutyl, 1-ethylpropyl, 1,2-dimethylpropyl, hexyl, isohexyl; 1,2-dimethylbutyl, heptyl, isoheptyl; 1-methylhexyl; 1,1-dimethyl, 2,3-dimethyl, 2,4-dimethyl or 3,3-dimethylpentyl; octyl, 1-methyl- or 3 -methyl-heptyl, 1,5-dimethyl- or 2,4-dimethylhexyl; 1,1,3,3-tetramethylbutyl, nonyl, 1-methyloctyl, decyl- or the dodecyl group; as an alkenyl group with 3 to 5 carbon atoms, the allyl; 1-methyl- or 2-methylallyl; 2- or 3-butenyl, 1,1-dimethylallyl, 3-methyl-2-butenyl group; as a cycloalkyl or lower alkyl-cycloalkyl group with a total of at most 7 carbon atoms, the cyclopropyl, cyclobutyl, cyclopentyl, cyclohexyl or cycloheptyl group, 1-methyl- or 2-methyl-cyclopropyl, 2,2-dimethylcyclopropyl, 1-methylcyclobutyl, 3,3-dimethylcyclobutyl; 2- or 3-methyl-cyclopentyl; 2-ethylcyclopentyl and 2-methyl-, 3-methyl- or 4-methylcyclohexyl group; as a cycloalkenyl or lower alkylcycloalkenyl group with a total of at most 7 carbon atoms, the 3-cyclopenten-1-yl; 2- or 3-cyclohexen-1-yl; 3-cyclohepten-1-yl, 2,2-dimethyl-3-cyclopenten-1-yl or 2-methyl-2-cyclohexen-1-yl group; as a phenylalkyl group with 7 to 9 carbon atoms, the benzyl, phenethyl, 3-phenylpropyl or α-methylphenethyl group; X as halogen of atomic number up to 35 is fluorine, chlorine or bromine; X as a lower alkyl group, the alkyl groups with at most 7 carbon atoms listed under $R_1$; as an alkyl group which is or is not interrupted by 1 or by 2 non-adjacent oxygen or sulphur atoms and contains a total of at most 7 carbon atoms, the methoxymethyl, ethoxymethyl, 2-ethoxyethyl, propoxymethyl,isopropoxymethyl, 3-methoxypropyl, 1-methyl-3-methoxypropyl, butoxymethyl, isobutoxymethyl, sec.butoxymethyl, 3-ethoxypropyl, 2-methoxypentyl, isopentoxymethyl, 2-methylbutoxymethyl, 1-ethyl-3-methoxypropyl, (2-methoxyethoxy)-methyl, (2-ethoxyethoxy)-methyl group or (2-butoxyethoxy)-methyl group, and the (methylthio)-methyl, (ethylthio)-methyl, (propylthio)-methyl, (isopropylthio)-methyl, 2-(methylthio)-ethyl, 2-(ethylthio-ethyl, 3-(methylthio)-propyl, [[2-(methylthio)-ethyl]-thio]-methyl, [[2-ethylthio)-ethyl]-thio]-methyl, [(2-methoxyethyl)-thio]-methyl or [2-(methylthio)-ethoxy]-methyl group; as an alkoxy or alkylthio group, which is or is not interrupted by 1 or by 2 non-adjacent oxygen or sulphur atoms, and contains a total of at most 7 carbon atoms, the methoxy, ethoxy, propoxy, isopropoxy, n-butoxy, isobutoxy, sec. butoxy, pentoxy, isopentoxy, 2,2-dimethylpropoxy, 1-methylbutoxy, 1-ethylpropoxy, 1,2-dimethylpropoxy, hexyloxy, isohexyloxy, 1,2-dimethylbutoxy, heptyloxy, isoheptyloxy, 1-methylhexyloxy, 2-methoxyethoxy, 2-ethoxyethoxy, 2-butoxyethoxy, 2-isopentoxyethoxy, 3-methoxypropoxy, 3-ethoxypropoxy, 3-isopropoxypropoxy, 2-(methylthio)-ethoxy, 2-(2-methoxyethoxy)-ethoxy, 2-(2-ethoxyethoxy)-ethoxy, 2-(2-propoxyethoxy)-ethoxy, (methylthio), (ethylthio), (propylthio), (isopropylthio), (butylthio), (tert.butylthio), (pentylthio), (isopentylthio), (hexylthio), (heptylthio), [[2-(methylthio)-ethyl]-thio], [[2-(ethylthio)-ethyl]-thio], [[2-(isopropylthio)-ethyl]-thio], [[2-(butylthio)-ethyl]-thio], [[3-(methylthio)-propyl]-thio], [2-(methoxyethyl)-thio], [[ 2-(ethylthio)-ethyl]-thio] or [[2-[[2-(methylthio)-ethyl]-thio]-ethyl]-thio] group; and as an alkanamido group, for example the formamido, propionamido, butyramido and especially the acetamido group. The radical Y is, in accordance with the definition of X, hydrogen or one of the substituents mentioned as examples of this symbol.

As a radical of the partial formula Ia, Y is, for example, the 1-aminoethyl, 2-aminopropyl, 2-(methylamino)-propyl, 3-aminopropyl, 2-(methylamino)-ethyl and above all the 2-aminoethyl group, and as a radical of the partial formula Ib it is one of the groups mentioned as examples of radicals of the partial formula Ia, of which the amino group is substituted by an acyl radical or thioacyl radical of the formula $R_4$—C(-Z)—, in which Z is oxygen or sulphur and $R_4$ can have, for example, the following meanings: As an alkyl group, the radicals, with at most 7 carbon atoms, mentioned as examples of $R_1$; as a chloroalkyl group, the 1-chloroethyl, 1-chloropropyl, 1-chlorobutyl, 1-chloropentyl, 1-chlorohexyl, 2-chlorohexyl or 1-chloroheptyl group; as an alkenyl group with 2 to 5 carbon atoms, the vinyl, 1-propenyl, allyl, isopropenyl, 1-butenyl, 2-butenyl, 2-methyl-1-propenyl, pentenyl or 1,2-dimethyl-1-propenyl group; as a cycloalkyl group or lower alkyl-cycloalkyl group with a total of at most 8 carbon atoms, the cyclopropyl, cyclopropylmethyl, cyclobutyl, cyclobutylmethyl, cyclopentyl, cyclopentylmethyl, cyclohexyl, 2-methylcyclohexyl, 4-methylcyclohexyl, cycloheptyl, or the cyclooctyl group; as a cycloalkenyl group or lower alkyl-cycloalkenyl group with a total of at most 8 carbon atoms, the 1-cyclopenten-1-yl, 2-cyclopenten-1-yl, 1-cyclohexen-1-yl, 2-cyclohexen-1-yl, 3-cyclohexen-1-yl, 1-methyl-3-cyclohexen-1-yl, 2-methyl-2-cyclohexen-1-yl, 3-methyl-2-cyclohexen-1-yl, 1-cyclohepten-1-yl, 2-cyclohepten-1-yl, 3-cyclohepten-1-yl, 2-cycloocten-1-yl, or 3-cycloocten-1-yl group; as a phenylalkyl group of 7 to 10 carbon atoms or a phenylalkenyl group of 8 to 10 carbon atoms, the benzyl, phenethyl, 3-phenylpropyl, or 4-phenylbutyl group, or, for example, the styryl group. The phenyl radical present as a substituent $R_4$ or the phenyl group present as a part of the two named types of radicals $R_4$ can be monosubstituted, disubstituted or trisubstituted and this substituent or these substituents can, in particular, be the following groups: Halogen up to atomic number 35, that is to say chlorine, fluorine or bromine; trifluoromethyl groups; alkyl groups with at most 4 carbon atoms, such as the methyl, ethyl, propyl, isopropyl, butyl, isobutyl, sec.butyl or tert.butyl group; hydroxyl groups or alkoxy or alkylthio groups each with at most 2 carbon atoms, that is to say the methoxy, ethoxy, methylthio or ethylthio group. Furthermore, $R_4$ can be, for example, the 2-furyl, 5-methyl-2-furyl, 2-thienyl, 3-thienyl, 5-methyl-2-thienyl, 2-pyridyl, 3-pyridyl, 4-pyridyl, 4-methyl- and 6-methyl-2-pyridyl, 2-methyl-, 4-methyl-, 5-methyl- and 6-methyl-3-pyridyl or 2-methyl- 4-pyridyl radical.

The new derivatives of imidazolidine of the general formula I, and their addition salts with inorganic and organic acids, possess valuable pharmacological properties, especially a hypoglycaemic activity, as can be demonstrated on metabolically normal rats after oral administration of doses from 30 mg/kg upwards and also on rats which have been placed in a metabolic state resembling diabetes through injection of Streptozotocin [compare A. Junod et al., Proc.Soc.Exp.Biol.Med. 126, 201–205 (1967)]. These findings characterise the new derivatives of imidazolidine of the general formula I, and their pharmaceutically acceptable addition salts with inorganic and organic acids as antidiabetics which can be used for the oral treatment of hyperglycaemia in mammals, and especially of diabetes mellitus.

The invention in particular relates to compounds of the formula I in which Het is a thienyl radical, or a heteroaromatic radical with 5 to 6 ring members including 1 or 2 nitrogen atoms, above all a pyridyl, pyrimidyl or imidazolyl radical, or a 1,3,4-thiadiazolyl radical, which radicals are unsubstituted or substituted in accordance with the definitions of X and Y given under the formula I, whilst $R_1$ and $R_2$ have the meaning indicated under the formula I, and their pharmaceutically acceptable acid addition salts. Further compounds to be singled out particularly are those of the formula I in which Y is a radical of the partial formula Ib whilst X has the meaning indicated under the formula I, but is, in particular, hydrogen or optionally a methyl or methoxy group, and $R_1$, $R_2$ and Het have the meaning indicated under the formula I. These compounds correspond to the formula XIII given later and embraced by the formula I. Further compounds of particular importance are those in which $R_1$ is a cycloalkyl or lower alkyl-cycloalkyl group with a total of at most 7 carbon atoms, above all the cyclopentyl or cyclohexyl group, and $R_2$ is the methyl group or above all is hydrogen, whilst Het, X and Y have the meaning indicated under the formula I.

The invention relates in particular to compounds of the formula I, which combine in themselves two or all of the above-mentioned structural characteristics. In these compounds, $R_1$ is a cycloalkyl or lower alkyl-cycloalkyl group with a total of at most 7 carbon atoms, above all the cyclopentyl or cyclohexyl group, and $R_2$ is the methyl group or above all hydrogen. Het is a thienyl, pyridyl or pyrimidinyl radical, and X is hydrogen, but X on a pyrimidinyl radical as the radical Het can also be the methyl or methoxy group. Y is a radical of the partial formula Ib, in which $R_3$, $R_4$, Z and m have the meaning indicated under this formula. Hence, all these compounds are embraced by the narrower general formula XIII given later.

Above all, the invention relates to compounds of the general formula I, in which $R_1$ has the narrower meaning which has just been given, and is above all cyclopentyl or cyclohexyl, and $R_2$ and X denote hydrogen and Het is a thienyl radical. Y in these compounds is a radical of the partial formula Ib, in which $C_mH_{2m}$ is an ethylene group and $R_3$ is hydrogen, whilst $R_4$ is an alkyl group with at most 5 carbon atoms, above all the propyl group, or a cycloalkyl group with at most 6 carbon atoms, and at the same time the radical Z is oxygen or sulphur, or $R_4$ is a methoxyphenyl group which is optionally chlorine-substituted in the ring, such as the 2-methoxyphenyl or 3-methoxyphenyl and 2-methoxy-5-chlorophenyl group, or is an optionally methyl-substituted, but preferably unsubstituted 2-thienyl, 2-furyl or 3-pyridyl radical, and the radical Z is oxygen. Most preferred as radicals $R_4$ are alkyl groups with 2 to 4 carbon atoms, above all the propyl group, together with oxygen as the radical Z. 1-[5-(2-Butyramido-ethyl)-2-thienylsulphonyl]-2-imino-3-cyclohexyl-imidazolidine may be mentioned as an example of this type of compound.

The abovementioned types of compound always also include the corresponding pharmaceutically acceptable addition salts with inorganic and organic acids.

According to the invention, the compounds of the general formula I and their acid addition salts are prepared by a. reacting a reactive functional derivative of a sulphonic acid of the general formula II $$Y'-\overset{X}{\underset{}{Het}}-SO_2-OH \qquad (II)$$

in which $Y'$ has the meaning indicated for Y under the formula I, with the exception of the radical of the partial formula Ia, and X and Het have the meaning indicated under the formula I, with a compound of the general formula III (III)

in which $R_1$ and $R_2$ have the meaning indicated under the formula I, or b. cyclising a compound of the general formula IV (IV)

in which $R_5$ denotes hydrogen, an arylmethyl, diarylmethyl or triarylmethyl group, the methyl group or the allyl group and X, Het, $R_1$ and $R_2$ have the meaning indicated under the formula I and $Y'$ has the meaning indicated under the formula II, by means of a reactive cyanic acid derivative, or c. condensing and cyclising a reactive ester of a compound of the general formula V (V)

with a compound of the general formula VI $$A_2 - NH_2 \qquad (VI)$$

in which formulae one of the symbols $A_1$ and $A_2$ denotes the radical $R_1$ defined under the formula I and the other denotes the radical of the partial formula Va $$Y'-\overset{X}{\underset{}{Het}}-SO_2 \qquad (Va)$$

in which X and Het have the meaning indicated under the formula I and $Y'$ has the meaning indicated under the formula II, and $R_2$ has the meaning indicated under the formula I, or d. condensing and cyclising a compound of the general formula VII (VII)

or a reactive ester of a compound of the general formula VIII (VIII)

in which formulae X, Het and $R_2$ have the meaning indicated under the formula I and $Y'$ has the meaning indicated under the formula II, with a compound of the general formula IX $$H-\overset{}{\underset{C\ \equiv\ N}{N-R_1}} \qquad (IX)$$

in which $R_1$ has the meaning indicated there under the formula I, or with an alkali metal derivative or alkaline earth metal derivative of such a compound, or e. cyclising, by heating, an addition salt of the general formula X (X)

in which Hal denotes halogen, especially chlorine or bromine, X, Het, $R_1$ and $R_2$ have the meaning indicated under the formula I and $Y'$ has the meaning indicated under the formula II, f. if desired, hydrolysing a compound of the general formula I, in which Y and optionally also X is an alkanamido group with 1 to 4 carbon atoms, or Y is a radical of the partial formula Ic

in which $R_6$ denotes hydrogen or an alkyl group with at most 4 carbon atoms, and $R_3$ and m, and also X, Het, $R_1$ and $R_2$, have the meaning indicated under the formula I, to give the corresponding compound of the general formula I, in which Y and optionally also X is an amino group, or to the corresponding compound of the general formula XI embraced by the general formula I

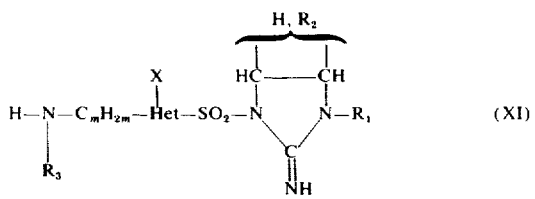

in which $R_3$, m, X, Het, $R_1$ and $R_2$ have the meaning indicated under the formula I, or g. if desired, reacting a compound of the general formula XI embraced by the general formula I and defined above, with a carboxylic acid or dithiocarboxylic acid of the general formula XII

in which $R_4$ and Z have the meaning indicated under the formula I, or with a reactive functional derivative of such an acid, to give a compound of the general formula XIII embraced by the general formula I

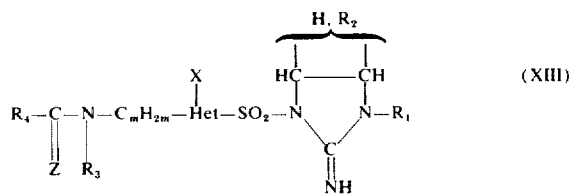

in which Het, $R_1$, $R_2$, X, m, Z, $R_3$ and $R_4$ have the meaning indicated under the general formula I, or h. if desired, reacting a compound of the general formula I in which X and/or Y denotes a hydroxyl group which is in the ortho-position and/or para-position to at least one ring nitrogen atom, Het is a heteroaromatic radical, with at least one ring nitrogen atom, which falls under the definition given below formula I, and $R_1$, $R_2$ and Y and X have the meaning indicated under the formula I, with a chloride or bromide of a mineral acid, or i. if desired, reacting a compound of the general formula I, in which X and/or Y denote a chlorine or bromine atom which is in the ortho- and/or para-position to at least one ring nitrogen atom, Het is a heteroaromatic radical, with at least one ring nitrogen atom, falling under the definition given below formula I and $R_1$, $R_2$ and Y and X have the meaning indicated under the formula I, with ammonia or with a metal compound of an alkanol or alkanethiol, both of which can be interrupted by 1 or 2 oxygen atoms or sulphur atoms and contain a total of at most 7 carbon atoms, and, if desired, converting a compound obtained in accordance with the processes defined above, of the general formula I or of the general formula XI or XIII embraced by the former, into an addition salt with an inorganic or organic acid.

Examples of suitable reactive functional derivatives of sulphonic acids of the general formula II for the reaction according to a) are the halides, especially the chlorides, or the anhydrides. The reaction according to (a) is preferably carried out in the presence of a water-miscible or water-immiscible inert organic solvent in the presence or absence of water, or exclusively in water. Suitable inert organic solvents are, for example, lower ketones, such as acetone or methyl ethyl ketone, ether-like liquids, such as ether, dioxane or tetrahydrofurane, hydrocarbons, such as benzene, toluene or xylene, and chlorinated hydrocarbons, such as methylene chloride. It is advantageous to add an acid-binding agent to the reaction solution. Examples of suitable agents of this kind are inorganic bases or salts, for example alkali metal hydroxides, alkali metal bicarbonates, alkali metal carbonates or alkali metal phosphates, such as the corresponding sodium compounds or potassium compounds. It is also possible to use organic bases such as, for example pyridine, trimethylamine or triethylamine, diisopropylethylamine or collidine, and these, added in excess, can also be employed as solvents.

Possible sulphonic acids of the general formula II are, for example, compounds in which the symbols X, Y' and Het represent the radicals listed earlier as examples. The most important group of functional derivatives of such sulphonic acids, the sulphonyl chlorides, can be prepared, for example, by reaction of heteroaromatic compounds corresponding to the defined meaning of Het, X and Y', with chlorosulphonic acid. The corresponding anhydrides are obtained, for example, by boiling sulphonic acids of the general formula II in excess thionyl chloride or heating the sulphonyl chlorides with anhydrous oxalic acid.

Substantial numbers of starting materials of the general formula III are known, and further such materials can be prepared analogously to the known compounds.

In the starting materials of the general formula IV for the reaction according to (b), $R_5$, as an arylmethyl, diarylmethyl or triarylmethyl group, is, for example, the benzyl, benzhydryl or trityl group. Examples of suitable reactive cyanic acid derivatives are, for example, cyanogen halides, such as cyanogen chloride or cyanogen bromide, or cyanic acid esters, especially cyanic acid phenyl ester. The reaction according to (b) is preferably carried out in the presence of a water-miscible or water-immiscible inert organic solvent, in the presence or absence of water. Suitable inert organic solvents are, for example, hydrocarbons, such as benzene, toluene or xylene, lower alkanols, such as methanol or ethanol, chlorinated hydrocarbons, such as methylene chloride, ether-like liquids, such as ether, dioxane or tetrahydrofurane, lower ketones, such as acetone or methyl ethyl ketone, carboxylic acid esters, such as ethyl acetate, carboxylic acid nitriles, such as acetonitrile, or sulphones, such as tetrahydrothiophene-1,1-dioxide. The reaction can be carried out in the presence or absence of an acid-binding agent. Suitable acid-binding agents are inorganic bases or salts, for example alkali metal hydroxides, alkali metal bicarbonates, alkali metal carbonates or alkali metal phosphates, such as the corresponding sodium compounds or potassium compounds. Furthermore, calcium carbonates, as well as calcium phosphates and magnesium carbonate, can also be employed.

Examples of suitable starting materials of the general formula IV are those compounds in which the symbols $R_1$, $R_2$, X, Y', Het and $R_5$ represent the radicals listed earlier as examples. Such starting materials can be obtained, for example, analogously to process (a) by reaction of the chlorides of sulphonic acids of the general formula II with ethylenediamines, 1,2-propanediamines or 1,2-butanediamines, of which one amino group is substituted by a radical corresponding to the definition of $R_1$ and optionally also a radical corresponding to the definition of $R_5$.

Reactive esters of compounds of the general formula V which are suitable for the process according to (c) are, for example, halides, especially chlorides or bromides, and also sulphonic acid esters, for example the o- or p-toluenesulphonic acid ester or the methanesulphonic acid ester. The condensation and cyclisation according to (c) is preferably carried out in a water-miscible or water-immiscible organic solvent in the presence or absence of water. As solvents it is possible to use alkanols, for example butanol, ether-like liquids, for example dioxane and diethylene glycol monomethyl ether, carboxylic acid amides, such as N,N-dimethylformamide, or sulphoxides, such as dimethylsulphoxide. It is advantageous to carry out the condensation in the presence of an acid-binding agent. As such, it is possible to use those compounds which are mentioned after the process according to (a) or, if in the starting material of the general formula VI $A_2$ is a radical $R_1$, also an excess of this starting material.

Examples of suitable reactive esters of compounds of the general formula V are the previously mentioned types of reactive esters of those compounds of the general formula V in which the symbols $R_2$ and $A_1$, that is to say $R_1$ and Het, X and Y', represent the radicals listed earlier as examples of these symbols. Some halides, especially bromides, of compounds of the general formula V, in which $A_1$ is a radical $R_1$, are known and others can be prepared analogously, for example by reaction of aziridines, 2-methylaziridines or 2-ethylaziridines, which are substituted in the 1-position in accordance with the definition of $R_1$, with a cyanogen halide, especially cyanogen bromide. Halides, especially bromides, of compounds of the general formula V, in which $A_1$ is a radical of the partial formula Va, are obtained, for example, by first allowing aziridine, 2-methylaziridine or 2-ethylaziridine to react with a cyanogen halide, especially cyanogen bromide, in ether, and reacting the resulting N-(2-halogenoalkyl)-cyanamide, especially N-(2-bromoalkyl)-cyanamide, with the chloride of a sulphonic acid of the general formula II, in which Het, X and Y' have the meaning indicated under the formula I or the formula II, for example in an aqueous acetone solution in the presence of an equimolar amount of sodium hydroxide.

Some starting materials of the general formula VI, in which $A_2$ is a radical of the partial formula Va, are known and others can be prepared analogously to the known compounds. Starting materials of the general formula VI, in which $A_2$ is a radical $R_1$, are also known, and in fact in larger numbers.

Suitable reactive esters of compounds of the general formula VIII for the reaction according to (d) are, for example, halides, especially chlorides or bromides, and also sulphonic acid esters, for example the o- or p-toluenesulphonic acid ester or the methanesulphonic acid ester. Examples of suitable alkali metal derivatives and alkaline earth metal derivatives of compounds of the general formula IX are sodium, potassium, lithium and calcium derivatives. The condensation and cyclisation according to (d) is carried out in an inert organic solvent, preferably in an ether-like solvent, such as, for example, diethyl ether, tetrahydrofurane, dioxane, anisole or ethylene glycol dimethyl ether, in a carboxylic acid amide, such as N,N-dimethylformamide, or in a sulphoxide, such as dimethylsulphoxide. If the cyanamide of the general formula IX is employed as such, it is advantageous to carry out the reaction in the presence of an acid-binding agent. As the acid-binding agent it is possible to use, for example, tertiary organic bases or, preferably, inorganic bases, such as sodium hydroxide or potassium hydroxide, and in that case the reaction can also be carried out, for example, in an alcohol, for example in an alkanol, such as butanol, or in diethylene glycol monomethyl ether, in the presence or absence of water.

Suitable starting compounds of the general formulae VII and IX, and compounds of the general formula VIII on which the reactive esters required as starting materials are based, are, for example, those in which the symbols Het, X, Y' and $R_1$ represent the radicals listed earlier. Starting compounds of the general formula VII are obtained, for example, by reaction of the chloride of a sulphonic acid of the general formula II, in which Het, X and Y' have the meaning indicated under the formula I or under the formula II, with aziridine, 2-methylaziridine or 2-ethylaziridine in the presence of an acid-binding agent, that is to say analogously to the process according to (a), whilst chlorides of compounds of the general formula VIII are obtained if the same reactants are reacted in the absence of an acid-binding agent, in an inert organic solvent. Some cyanamides of the general formula IX are known and others can be prepared analogously to those known, for example by reaction of cyanogen bromide with primary amines, which correspond to the general formula VI with a radical $R_1$, according to the definition, as $A_2$, in situ, immediately prior to their further condensation with compounds of the general formula VII or VIII. The cyanamides first obtained can be converted, again in situ, into their metal derivatives, for example into their sodium derivatives by means of sodium hydride.

The cyclisation of addition salts of the general formula X according to (e) can be effected by heating in a solvent, or without a solvent. Suitable solvents are higher-boiling liquids, for example ethers, such as diethylene glycol dimethyl ether, or carboxylic acid amides, such as N,N-dimethylformamide.

Examples of suitable starting materials for the cyclisation according to (e) are addition salts of the general formula X in which Hal is preferably chlorine or bromine and the symbols Het, X and Y' and $R_1$ and $R_2$ represent the radicals listed earlier as examples of these symbols. Such compounds can be prepared, for example, by condensing chlorides of sulphonic acids of the general formula II with disodium cyamide in water to give sodium derivatives of the corresponding N-cyanosulphonamides and reacting the latter subsequently with N-(2-chloroethyl)-amine hydrochlorides or N-(2-bromoethyl)-amine hydrobromides or hydrochlorides which are substituted at the nitrogen atom by a radical $R_1$ which accords with the definition and are optionally substituted at a carbon atom by a methyl or ethyl group.

The hydrolysis according to (f) of compounds of the general formula I, in which Y and optionally also X is an alkanamido group with 1 to 4 carbon atoms, especially the formamido or acetamido group, or Y is a radical of the partial formula Ic, in which $R_6$ is preferably hydrogen or a methyl group, whilst X is a radical which corresponds to the definition given under the formula I but is preferably hydrogen or, if a primidinyl radical is present as Het, is optionally a methyl or methoxy group, is preferably carried out in an acid medium, for example by warming, preferably boiling, in dilute aqueous or aqueous-alkanolic, for example aqueous-methanolic or aqueous-ethanolic, hydrochloric acid. However, the hydrolysis can also be carried out in a basic medium, for example by warming in dilute aqueous or aqueous-alkanolic sodium hydroxide solution or potassium hydroxide solution. The starting materials required, which already fall under the general formula I, can be prepared in accordance with one of the processes mentioned under (a) to (e).

The reaction of free carboxylic acids of the general formula XII with compounds of the general formula XI according to (g) is carried out, for example, in the presence of a carbodiimide such as, for example, dicyclohexyl-carbodiimide, in an inert organic solvent, such as, for example, tetrahydrofurane or one of the solvents mentioned later. Possible reactive functional derivatives of carboxylic acids and dithiocarboxylic acids of the general formula XII for the acylation according to (g) are, in particular, acid halides, especially acid chlorides, acid anhydrides and mixed acid anhydrides, in particular those with carbonic acid half-esters, such as of ethoxyformic acid, or lower alkyl esters, such as the methyl or ethyl ester or benzyl ester, as well as activated esters, such as p-nitrophenyl ester and the cyanomethyl ester. The reactions according to (g) are preferably carried out at temperatures between approx. 0° and 140°C, depending on the reactivity of the acid derivatives employed, in an inert organic solvent, for example a hydrocarbon, such as benzene, toluene or xylene, an ether-like solvent, such as ether, dioxane or tetrahydrofurane, a chlorinated hydrocarbon, such as methylene chloride, or a lower ketone, such as, for example, acetone or methyl ethyl ketone. In reactions with acid halides or anhydrides it is advantageous to add an acid-binding agent to the reaction solution. Examples of suitable agents are organic bases, such as, for example, pyridine, trimethylamine or triethylamine, N,N-diisopropylethylamine or collidine, which, when added in excess, can also be employed as solvents. Furthermore, it is also possible to use inorganic bases or salts, for example alkali metal hydroxides, alkali metal bicarbonates, alkali metal carbonates or alkali metal phosphates, such as the corresponding sodium compounds or potassium compounds.

Suitable reactive functional derivatives of dithiocarboxylic acids falling under the general formula XII are, in particular, their lower alkyl esters, for example the methyl esters, and above all the benzyl esters. These are reacted in the presence or absence of one of the above-mentioned inert organic solvents, and in the indicated temperature range, but preferably at approx. 80°C, with compounds of the general formula XII. The dithiocarboxylic acid esters required are in part known [compare C. S. Marvel et al., J.Amer.Chem.Soc. 77, 5997–5999 (1955)] and others are prepared analogously by first reacting the corresponding nitriles with the corresponding mercaptans, especially benzylmercaptan, in the presence of hydrogen chloride to give the corresponding iminothiocarboxylic acid ester hydrochlorides and treating the latter, in pyridine, with hydrogen sulphide at approx, 0°C.

Carboxylic acids of the general formula XII and reactive functional derivatives thereof are known in large numbers and others can be prepared analogously to the known compounds. For example, the starting compounds of the general formula XI are prepared by a hydrolysis in accordance with the process mentioned above under (f).

For replacing hydroxyl groups X and/or Y by chlorine or bromine in accordance with the reaction mentioned under (h), halides of phosphoric acid, for example, are used, above all phosphorus oxychloride, phosphorus pentachloride or their mixtures or phosphorus oxybromide, phosphorus pentabromide or their mixtures, at elevated temperatures, for example 70° to 150°C or up to the boiling point of the phosphorus oxychloride, or up to approx. 100°C when using phosphorus pentabromide. The reaction medium can optionally be an excess of phosphorus oxychloride or phosphorus oxybromide, a hydrocarbon, such as, for example, toluene or xylene, or another organic solvent, such as, for example, N,N-dimethylformamide, N,N-dimethylaniline, N,N-diethylaniline or pyridine. The starting compounds which already fall under the general formula I can be prepared in accordance with the processes mentioned under (a) to (g).

Metal compounds of alkanols and alkanethiols which accord with the definition, which are suitable for the reaction with compounds of the general formula I, which contain a reactive chlorine or bromine atom as X and/or Y, in accordance with (i), are, in particular, alkali metal compounds, for example the sodium compounds. The solvents used are either the alkanols on which the metal compounds are based, or inert organic solvents, such as, for example, N,N-dimethylformamide or dimethylsulphoxide. Reactions with metal compounds of alkanethiols which accord with the definition can also be carried out in lower alkanols, for example methanol or ethanol. The reactions with the metal compounds are carried out, for example, at room temperature or, if necessary, with warming, if appropriate in a closed vessel. Reactions according to (i) with ammonia are carried out, for example, in a lower alkanol, such as methanol or ethanol preferably with warming, if necessary up to approx. 130°–180°C in a closed vessel. The starting compounds which already fall under the general formula I can be prepared, for example, in accordance with the processes mentioned under (a) to (g), optionally followed by replacement of hydroxyl groups X and/or Y by chlorine or bromine according to (h).

The present invention also relates to those modifications of the processes mentioned under (a) to (i) and of their preliminary stages, in which a process is discontinued at any stage or in which a compound occurring as an intermediate product at any stage is used as the starting material and the missing steps are carried out, or a starting material is formed under the reaction conditions or used in the form of a salt, if appropriate. If the starting materials required are optically active, it is possible to employ them either as racemates or as isolated antipodes or, if diastereomerism exists, either as racemate mixtures or as specific racemates or again as isolated antipodes. Such starting materials can also, where appropriate, be used in the form of salts.

Where end products are obtained as racemates or racemate mixtures, they can, if desired, be separated, and resolved into their antipodes, within the scope of the present invention.

The compounds of the general formula I obtained in accordance with the process of the invention are converted, if desired, in the usual manner into their addition salts with inorganic and organic acids. For example, the acid desired as the salt component is added to a solution of a compound of the general formula I in an organic solvent. Preferably, organic solvents in which the salt is produced is sparingly soluble are chosen for the reaction, so that the salt can be separated off by filtration. If necessary, the crystallisation of the salt is brought about, or completed, by addition of a second solvent. Examples of such solvents or mixtures are ethyl acetate, methanol, ether, acetone, methyl ethyl ketone, acetone-ether, acetone-ethanol, methanol-ether or ethanol-ether.

For use as medicaments it is possible to employ, instead of the free bases, pharmaceutically acceptable acid addition salts, that is to say salts with acids of which the anions are non-toxic at the dosages in question. Furthermore, it is an advantage if the salts to be used as medicaments can be crystallised well and are non-hygroscopic or only slightly hygroscopic. To form salts with compounds of the general formula I it is possible to employ, for example, hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicyclic acid, phenylacetic acid, mandelic acid and embonic acid.

The new derivatives of imidazolidine corresponding to the general formula I, and their pharmaceutically acceptable acid addition salts, are preferably administered perorally. The daily dosages vary between 1.0 and 100 mg/kg for warm-blooded animals. Suitable unit dosage forms, such as dragées or tablets, preferably contain 1 to 100 mg of an active compound according to the invention, that is to say of a compound of the general formula I or of a pharmaceutically acceptable acid addition salt of such a compound. To prepare such unit dosage forms, the active compound is combined with solid pulverulent excipients such as lactose, sucrose, sorbitol or mannitol, starches, such as potato starch, maize starch or amylopectin, and also laminaria powder or citrus pulp powder, cellulose derivatives or gelatine, optionally with the addition of lubricants, such as magnesium stearate or calcium stearate or polyethylene glycols, to give tablets or to give dragée cores. The latter are coated, for example with concentrated sugar solutions, which can additionally contain, for example, gum arabic, talc and/or titanium dioxide, or with a lacquer dissolved in readily volatile organic solvents or solvent mixtures. Dyestuffs can be added to these coatings, for example to characterise different doses of active compound. Further suitable oral unit dosage forms are syrups or shakes and also gelatine push-fit capsules as well as soft, sealed capsules of gelatine and a plasticiser, such as glycerol. The former preferably contain the active compound as granules mixed with lubricants, such as talc or magnesium stearate, and optionally with stabilisers, such as sodium metabisulphite or ascorbic acid.

The instruction which follows is intended to explain the preparation of tablets in more detail:

250.0 g of 1-[5-(2-butyramido-ethyl)-2-thienylsulphonyl]-2-amino-3-cyclohexyl-imidazolidine are mixed with 500 g of lactose and 292 g of potato starch, and the mixture is moistened with an alcoholic solution of 8 g of gelatine and granulated through a sieve. After drying, 60 g of potato starch, 60 g of talc, 10 g of magnesium stearate and 20 g of highly disperse silicon dioxide are mixed in and the mixture is pressed to give 10,000 tablets each weighing 120 mg and containing 25 mg of active compound, which can optionally be provided with breaking grooves for more accurate selection of the dosage.

The examples which follow explain the preparation of the new compounds of the general formula I and of previously unknown starting compounds in more detail, but are not intended in any way to restrict the scope of the invention.

EXAMPLE 1 a. 20 ml (0.02 mol) of 1 N sodium hydroxide solution are added dropwise over the course of 10 minutes, whilst stirring, to a mixture of 2.04 g (0.01 mol) of 1-cyclohexyl-2-imino-imidazolidine hydrochloride and 2.96 g (0.01 mol) of 5-(2-butyramido-ethyl)-2-thiophenesulphonyl chloride in 45 ml of water-acetone (1:2), at 25°C. In the course thereof, the reaction temperature rises to 33°C. The reaction mixture is stirred for a further 18 hours at 24°–25°C and the acetone is then evaporated off with the aid of a rotary evaporator. The oil-water mixture which remains is extracted twice with 30 ml of ethyl acetate at a time. The extracts are washed with 20 ml of saturated sodium chloride solution, then combined, dried over sodium sulphate and evaporated in vacuo. The residue is chromatographed on a column of 120 g of silica gel which is eluted with a mixture of chloroform and methanol (95:5). The eluate is evaporated with the aid of a rotary evaporator and the residue is recrystallized from toluene. Colourless crystals of 1-[5-(2-butyramido-ethyl)-2-thienylsulphonyl]-2-imino-3-cyclohexyl-imidazolidine of melting point 121°–125°C are obtained.

The starting compound, 5-(2-butyramido-ethyl)-2-thiophenesulphonyl chloride, is prepared as follows:

b. A solution of 5.33 g (0.05 mol) of butyryl chloride in 20 ml of absolute benzene is added dropwise over the course of 40 minutes to a mixture of 6.35 g (0.05 mol) of 2-(2-aminoethyl)-thiophene [compare W. Herz and Lin Tsai, J.Am.Soc. 77, 2529 (1955)], 5.55 g (0.055 mol) of triethylamine and 100 ml of absolute benzene at 25°C, whilst stirring. A weakly exothermic reaction occurs. The reaction mixture is stirred further for 18 hours at 20°C, 50 ml of 1 N potassium bicarbonate solution and 50 ml of ethyl acetate are added, and the stirring is continued for a further 25 minutes. The aqueous phase is then separated off. The organic phase is washed 3 times with 30 ml of water at a time, twice with 20 ml of 2 N hydrochloric acid at a time and three times with 20 ml of saturated sodium chloride solution at a time, and is dried over sodium sulphate and evaporated in vacuo. The oil which remains is chromatographed on a column of 360 g of silica gel. Elution is carried out with a mixture of toluene and ethyl acetate (1:1). Of 6 fractions each of 200 ml, the last four fractions are combined and evaporated. The oil which remains is distilled at an air bath temperature of 160°–180°C. The resulting 2-(2-butyramido-ethyl)-thiophene boils at 140°C/0.05 mm Hg.

c. 6.6 ml (0.100 mol) of chlorosulphonic acid are cooled in an ice bath to 4°C whilst stirring, and 3.35 g (0.017 mol) of 2-(2-butyramido-ethyl)-thiophene are then added over the course of 15 minutes in such a way that the reaction temperature does not rise above 8°C. The ice bath is then removed and the reaction mixture is stirred for 30 minutes at 28°–30°C and then poured, whilst stirring, onto 100 g of ice under which there is a layer of 50 ml of methylene chloride. The methylene chloride phase is separated off and the aqueous phase is extracted with a further 50 ml of methylene chloride. The combined extracts are washed with 50 ml of concentrated sodium chloride solution, dried over sodium sulphate and evaporated at 40°C bath temperature with the aid of a rotary evaporator. The crude 5-(2-butyramido-ethyl)-2-thiophenesulphonyl chloride is obtained.

EXAMPLE 2

20.4 g of 1-cyclohexyl-2-imino-imidazolidine hydrochloride are added, whilst stirring, to a solution of 17 g of sodium hydroxide in 170 ml of water. 23.5 g of 3-pyridinesulphonyl chloride are then added in portions to the reaction mixture, during which the reaction temperature rises from 25° to 45°C, and the mixture is then stirred additionally for 30 minutes at 90°C. After cooling, the reaction product which has precipitated is filtered off, washed with water and then with isopropanol and recrystallised from isopropyl acetate. The resulting 1-(3-pyridylsulphonyl)-2-imino-3-cyclohexyl-imidazolidine melts at 133°–134°C.

EXAMPLE 3

14.1 g of 1-cyclohexyl-2-imino-imidazolidine hydrochloride are added, whilst stirring, to a solution of 11.8 g of sodium hydroxide in 120 ml of water. A solution of 15.0 g of 5-chloro-2-thiophenesulphonyl chloride in 60 ml of acetone is then added dropwise to the reaction mixture over the course of 30 minutes at 20° to 30°C, whilst stirring. The reaction mixture is then stirred further at an oil temperature of about 90°C whilst at the same time distilling off the acetone through a bent tube. Whilst so doing, the internal temperature should rise from 70° to 90°C over the course of 1 hour. After cooling, the reaction product which has precipitated is filtered off, washed with water and recrystallised from 60 ml of isopropanol. The resulting 1-[(5-chloro-2-thienyl)-sulphonyl]-2-imino-3-cyclohexyl-imidazolidine melts at 117°–118°C.

EXAMPLE 4

10.2 g of 1-cyclohexyl-2-imino-imidazolidine hydrochloride are added, whilst stirring, to a solution of 8.5 g of sodium hydroxide in 85 ml of water. 1-Methylimidazole-2-sulphonyl chloride, melting at 70°–72°C and prepared by oxidative chlorination of 20.0 g of 1-methylimidazole-2-thiol [compare R. O. Roblin, Jr. and J. W. Clapp, J.Am.Chem.Soc. 72, 4890 (1950)] are then added in portions to the reaction mixture. The whole is then stirred for a further 30 minutes, at 90°C. After cooling, the reaction mixture is extracted three times with 100 ml of chloroform at a time. The combined extracts are twice washed with 50 ml of water at a time, dried with anhydrous magnesium sulphate and evaporated. The viscous oil which remains is chromatographed on a column of 340 g of silica gel. Elution is carried out with ethyl acetate and fractions of approx. 500 ml are collected. Fractions 7 to 14 are combined and evaporated. The pure 1-[(1-methylimidazol-2-yl)-sulphonyl]-2-imino-3-cyclohexylimidazolidine which remains melts at 91°–92°C.

EXAMPLE 5

8.7 g of 1-cyclohexyl-2-imino-imidazolidine hydrochloride are added, whilst stirring, to a solution of 7.3 g of sodium hydroxide in 73 ml of water. 5-Acetamido-1,3,4-thiadiazole-2-sulphonyl chloride, prepared by oxidative chlorination of 11.3 g of 5-acetamido-1,3,4-thiadiazole-2-thiol and melting at about 200°C, with decomposition, is then added in portions to the reaction mixture. Furthermore, 40 ml of acetone are added to the reaction mixture, which is then stirred for a further 3 hours at room temperature and clarified by filtration using diatomaceous earth, and the filtrate is adjusted to a pH value of about 5 with 19% strength hydrochloric acid. 1-[(5-Acetamido-1,3,4-thiadiazol-2-yl)-sulphonyl]-2-imino-3-cyclohexyl-imidazolidine, which precipitates in fine crystals, is filtered off, washed with water and dried. It melts at 277°–279°C (decomposition).

What we claim is:
1. An imidazolidine compound of the formula I

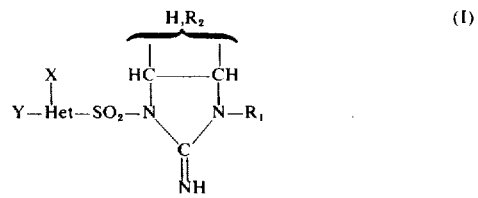

in which
Het is a thienyl radical,
$R_1$ denotes an alkyl group with at most 12 carbon atoms, an alkenyl group with 3 to 5 carbon atoms, a cycloalkyl, lower alkyl-cycloalkyl, cycloalkenyl or lower alkyl-cycloalkenyl group, each of which of at most 7 carbon atoms, or 7 to 9 carbon atoms,
$R_2$ denotes hydrogen, or the methyl or ethyl group,
X denotes hydrogen, halogen up to atomic number 35, an alkyl group which is or is not interrupted by 1 or by 2 non-adjacent oxygen or sulphur atoms and contains a total of at most 7 carbon atoms, or the hydroxyl group, the amino group or an alkanamido group with at most 4 carbon atoms, and
Y has the meaning of X or denotes a radical of the partial formula Ia or Ib

in which
$m$ denotes 2 or 3,
Z denotes oxygen,
$R_3$ denotes hydrogen or the methyl group, $R_4$ denotes an alkyl or chloroalkyl group with at most 7 carbon atoms, an alkenyl group with 2 to 5 carbon atoms, a cycloalkyl, lower alkyl-cycloalkyl, cycloalkenyl or lower-cycloalkenyl group, each of which with a total of at most 8 carbon atoms, a phenyl group, a phenylalkyl group of 7 to 10 carbon atoms or a phenylalkenyl group of 8 to 10 carbon atoms, whereby the phenyl group present as $R_4$ or as a part of $R_4$ is unsubstituted or substituted by one to three substituents selected from the group consisting of halogen up to atomic number 35, trifluoromethyl, alkyl with at most 4 carbon atoms, hydroxy, alkoxy with at most 2 carbon atoms and alkylthio with at most 2 carbon atoms, and the pharmaceutically acceptable addition salt of the compound of formula I with inorganic or organic acids.

2. A compound according to claim 1 having the formula I, in which Het is a thienyl radical, X is hydrogen, Y is a radical of the partial formula Ib given in claim 1, in which $C_mH_{2m}$ is the ethylene group, $R_3$ is hydrogen, $R_4$ is an alkyl group with at most 5 carbon atoms, or a cycloalkyl group with at most 6 carbon atoms, and at the same time the radical Z is oxygen, or $R_4$ is a methoxyphenyl or a methoxyphenyl group chlorine-substituted in the ring, and at the same time Z is oxygen, and $R_1$ is a cycloalkyl or lower alkyl-cycloalkyl group with a total of at most 7 carbon atoms, and $R_2$ is hydrogen, and their pharmaceutically acceptable addition salts with inorganic and organic acids.

3. A compound according to claim 1 having the formula I, in which Het is a thienyl radical, X is hydrogen, Y is a radical of the partial formula Ib given in claim 1, in which $C_mH_{2m}$ is the ethylene group, $R_3$ is hydrogen, $R_4$ is an alkyl group with 2 to 4 carbon atoms, and Z is oxygen, and $R_1$ is the cyclopentyl or cyclohexyl group, and $R_2$ is hydrogen, and their pharmaceutically acceptable additions salts with inorganic and organic acids.

4. A compound according to claim 1 which is 1-[5-(2-butyramido-ethyl)-2-thienylsulphonyl]-2-imino-3-cyclohexylimidazolidine and its pharmaceutically acceptable addition salts with inorganic or organic acids.

5. A compound according to claim 1 which is 1[(5-chloro-2-thienyl)-sulphonyl]-2-imino-3-cyclohexylimidazolidine and its pharmaceutically acceptable addition salts with inorganic or organic acids.

* * * * *